US008420392B2

(12) United States Patent
Kawase et al.

(10) Patent No.: US 8,420,392 B2
(45) Date of Patent: Apr. 16, 2013

(54) METHOD FOR CULTURING HUMAN PERIOSTEUM

(75) Inventors: Tomoyuki Kawase, Niigata (JP); Kazuhiro Okuda, Niigata (JP)

(73) Assignee: Niigata University, Niigata-Shi (JP)

( * ) Notice: Subject to any disclaimer, the term of this patent is extended or adjusted under 35 U.S.C. 154(b) by 384 days.

(21) Appl. No.: 12/674,609

(22) PCT Filed: Aug. 22, 2008

(86) PCT No.: PCT/JP2008/065050
§ 371 (c)(1),
(2), (4) Date: Feb. 22, 2010

(87) PCT Pub. No.: WO2009/025374
PCT Pub. Date: Feb. 26, 2009

(65) Prior Publication Data
US 2011/0045588 A1    Feb. 24, 2011

(30) Foreign Application Priority Data
Aug. 23, 2007    (JP) ................................. 2007-217340

(51) Int. Cl.
*C12N 5/071* (2010.01)
(52) U.S. Cl.
USPC ........................................................ 435/366
(58) Field of Classification Search .................. 435/366
See application file for complete search history.

(56) References Cited

U.S. PATENT DOCUMENTS
6,268,119 B1 *  7/2001  Sumita et al. ...................... 435/2

FOREIGN PATENT DOCUMENTS
| JP | 2003-052365 | A | 2/2003 |
| JP | 2003-055237 | A | 2/2003 |
| JP | 2003052365 | * | 2/2003 |
| JP | 2005-205074 | A | 8/2005 |
| JP | 2005205074 | * | 8/2005 |
| JP | 2006-289062 | A | 10/2006 |
| JP | 2008-212265 | A | 9/2008 |
| JP | 2008-295420 | A | 12/2008 |

OTHER PUBLICATIONS

Sakai et al. Transplantation of mesenchymal stem cells embedded in Atelocollagen gel to the intervertebral disc: a potential therapeutic model for disc degeneration. Biomaterials. 2003;24:3531-3541.*
Mizuno et al. A novel approach to regenerating periodontal tissue by grafting autologous cultured periosteum. Tissue Engineering. 2006;12(5):1227-1236.*
Clark et al. TGF-b1 stimulates cultured human fibroblasts to proliferate and produce tissue-like fibroplasia: A fibronectin matrix-dependent event. Journal of Cellular Physiology. 1997;170:69-80.*
Minoru Ueda, "Repair of bone defects using TGF-beta and FGF," Tissue Engineering, 2003, pp. 137-139.
Seiji Furukawa et al., "Production of cartilage matrix by house rabbit bone marrow-derived mesenchymal stem cells in collagen gel culture—the influence of supplementing TGF-beta1 and FGF-2 in monolayer culture," The Journal of the Japanese Orthopaedic Association, 2002, vol. 76, No. 8, pp. S1106 (2-H2-29).
Kazuhiro Okuda et al., "Periodontal Tissue Regeneration: Regeneration of Periodontal Tissue by Using Cultured Periosteal Sheet," Tissue Engineering, Jun. 27, 2007, pp. 212-219.
Kenji Kusumoto et al., "The Current Status and Future Prospects of Bone Regeneration," PEPARS, May 25, 2007, No. 15, pp. 84-89.
Kanoko Yamamiya et al., "Cultured Periosteum Combined with Platelet-Rich Plasma and a Porous Hydroxyapatite Graft for the Treatment of Intrabony Periodontal Defects in Humans—Case Report-," The Japanese Society of Periodontology Gakujutsu Taikai Program Oyobi Koen Shorokushu, 2006, vol. 49th Shunki, pp. 204.

* cited by examiner

*Primary Examiner* — Ruth Davis
*Assistant Examiner* — Lynn Y Fan
(74) *Attorney, Agent, or Firm* — McDermott Will & Emery LLP

(57) ABSTRACT

The present invention provides a method for forcingly culturing a piece of human periosteum tissue in a shorter culture period, the method including the steps of: (1) placing a periosteum piece dissected from a patient on a culture dish containing no culture solution; (2) dropping platelet-rich plasma collected from the patient onto the surface of the periosteum piece on the culture dish and coagulating the platelet-rich plasma so as to cover the surface of the periosteum piece; (3) adding a first culture medium to the culture dish and growing the culture; and (4) growing the culture in a second culture medium containing a basic fibroblast growth factor and no platelet-rich plasma, after the step (3).

3 Claims, 3 Drawing Sheets

METHOD FOR CULTURING HUMAN PERIOSTEUM

CROSS REFERENCE TO RELATED APPLICATIONS

The present application is the U.S. National Phase of International Patent Application Serial No. PCT/JP2008/065050, filed Aug. 22, 2008, which claims priority to Japanese Patent Application Serial No. 2007-217340, filed Aug. 23, 2007, both of which are hereby incorporated by reference in their entireties.

TECHNICAL FIELD

The present invention relates to a method for culturing autologous periosteum used for regenerative medicine, and specifically to a method for culturing autologous periosteum to be used for periodontal tissue regeneration therapy.

BACKGROUND ART

In Japan, about 80% of adults are suffering from periodontal disease. It is no exaggeration to say that periodontal disease is a national disease. With the progress of periodontal disease, alveolar bone is destroyed, which results in the loss of teeth. The current periodontal therapy is intended to remove dental plaque, dental calculus, and defective granulation which cause inflammation, thereby facilitating spontaneous regeneration of new periodontal tissues. A therapy to remove the causes of inflammation can prevent the progress of periodontal disease, but cannot regenerate lost tissues. In order to regenerate the lost alveolar bone, a cell-based therapy is used for the regeneration of periodontal tissues through autologous transplantation. In the cell-based therapy, adherent cells are selected as osteoblast precursor cells from the bone marrow stem cells of a patient, and are transplanted together with a cell-supporting scaffold, which is called an artificial substrate, thereby drawing out the inherent regenerating potential of the patient's cells. The cell-based therapy has been extensively performed at Niigata University Hospital (Patent Documents 1 and 2), and found to achieve significant regenerative effect.

Patent Document 1: Japanese Patent Application No. 2007-051153
Patent Document 2: Japanese Patent Application No. 2007-147906

DISCLOSURE OF INVENTION

Problems to be Solved by the Invention

In the prior art, however, it takes some 45 days to dissect a periosteum piece from a patient, to grow a periosteal sheet in culture, and to transplant the sheet. The period of time required for cell processing, that is, the culture period is too long for the patient, and hinders the increase of the number of cases treated in a medical institution, because culturing facilities are occupied for a longer period by a single patient. In addition, the longer the culture period, the more likely contamination and mix-up of the samples are to occur. This is the reason why the cell-based therapy is not yet popular, even though the therapy is highly beneficial. Therefore, there is a need for developing a method for forcingly culturing a piece of human periosteum tissue in a shorter culture period.

Means for Solving the Problem

The present invention provides a method for culturing a piece of human periosteum tissue, comprising the steps of: (1) placing a piece of the periosteum dissected from a patient on a culture dish containing no culture solution; (2) dropping platelet-rich plasma collected from the patient onto the surface of the periosteum piece on the culture dish and coagulating the platelet-rich plasma so as to cover the surface of the periosteum piece; (3) growing cells by adding a first culture medium to the culture dish; and (4) growing the cultured cells in a second culture medium containing basic fibroblast growth factor and no platelet-rich plasma, after the step (3). In the step (3) of the method for culturing the piece of human periosteum tissue according to the present invention, the culture may be grown in a first culture medium containing a transforming growth factor beta.

The transforming growth factor beta may be transforming growth factor beta 1.

In the step (1) of the method for culturing the piece of human periosteum tissue according to the present invention, the periosteum piece dissected from a patient may be subjected to the lysis of erythrocytes, washing with normal saline solution, followed by culturing in the first culture medium.

In the method for culturing the piece of human periosteum tissue according to the present invention, the step (4) may be followed by a step (5) of growing the culture in a third culture medium containing an osteoblast differentiation inducing agent.

In the step (5) of the method for culturing the piece of human periosteum tissue according to the present invention, the osteoblast differentiation inducing agent may contain dexamethasone, vitamin C, and β (beta)-glucerophosphate.

The present invention provides human periosteum-derived cells cultured by any of the methods for culturing the piece of human periosteum tissue of the present invention.

The present invention provides human periosteum-derived osteoblasts cultured by any of the methods for culturing the piece of human periosteum tissue of the present invention including the step of growing the culture in a third culture medium containing an osteoblast differentiation inducing agent.

The present invention provides an tissue-engineered bone formed from the human periosteum-derived osteoblasts of the present invention.

The present invention provides a use of osteoblasts including the step of embedding the human periosteum-derived osteoblasts of the present invention in a substrate, and mineralizing therein.

Regenerative therapies are broadly classified into the following three types: transplantation in addition with growth factor(s) of a substrate (cell-supporting scaffold) alone, of cells alone, and of a combination of a substrate and cells. The transplantation of a combination of a substrate and cells is further classified into two types: transplantation immediately after the collection of cells and transplantation after cell processing in vitro. Cultured artificial bone is transplanted by the latter method; cells are enhanced in vitro to be "intelligent" enough for expressing osteogenic potential, and then transplanted thereby achieving therapeutic effect comparable to that of autologous bone transplantation. The method for culturing periosteum according to the present invention comprises culturing in a test tube a human bone tissue, specifically a piece of human periosteum tusse dissected from a patient thereby proliferating periosteum-derived cells, and then differentiating them into osteoblasts.

The periosteum piece of the present invention refers to a piece of periosteum collected from the periosteum covering any hard tissue of the patient. The periosteum piece of the present invention may be collected from the surface of subgingival alveolar bone. The shape and size of the periosteum piece of the present invention are not particularly limited. However, the periosteum piece need not be so large for the purpose of obtaining a cultured periosteal sheet formed on a culture dish by the cells migrated from the piece of periosteum tissue. The size is preferably in the range from 10 mm×10 mm to 1 mm×1 mm, and more preferably about 5 mm×5 mm.

The normal saline solution of the present invention refers to a 0.9% NaCl aqueous solution, a Ringer's solution, a phosphate-buffered saline solution (hereinafter referred to as "PBS"), or any other similar isosmotic solution to human periosteum-derived cells. The normal saline solution of the present invention may or may not contain a pH buffer such as a phosphate buffer, a bicarbonate buffer, a Hepes buffer, or any other similar buffers. The normal saline solution of the present invention contains a balanced salt solution formulated by, for example, Tyrode, Earl, Hank, or Dulbecco. The normal saline solution of the present invention has been sterilized by autoclaved sterilization or filtration sterilization through a filter with 0.22μ micro)m pore diameter.

The culture medium may be any culture solution as long as it is supplemented with platelet-rich plasma, a basic fibroblast growth factor or an osteoblast differentiation inducing agent, which will be described later, together with 10% fetal bovine serum, thereby proliferating and differentiating the human periosteum-derived cells. The culture medium is preferably Medium 199. In cases where the cells cultured by the method for culturing the piece of human periosteum tusse according to the present invention are finally returned to the body of the patient from which the cells have been collected, the medium preferably contains a fetal bovine serum collected in Australia where there have been no BSE outbreaks, thereby avoiding the risk of infection to BSE. In addition, the basic fibroblast growth factor and osteoblast differentiation inducing agent are preferably preparations produced by recombinant DNA technologies, rather than preparations purified from animals. The culture media of the present invention may contain 25 μg/mL vitamin C or ascorbic acid, 100 unit/mL penicillin G potassium salt as an antibacterial agent, 0.1 mg/mL streptomycin, and 0.25 μg/mL amphotericin B. The culture media of the present invention have been sterilized by autoclaved sterilization or filtration sterilization through a filter with 0.22 μm pore diameter.

The first culture medium of the present invention contains platelet-rich plasma. The platelet-rich plasma is prepared in accordance with, for example, Okuda, K. et al., J. Periodontol. (2003) 849-857, or Japanese Patent Application Publication No. 2004-201799. In brief, fresh whole blood collected from a patient is poured in 10-mL centrifuge tubes containing an anticoagulant comprising citric acid and glucose, and centrifuged with a swing bucket rotor having a shortest axis of about 57 mm and a longest axis of about 140 mm at 2,400 rpm for 10 minutes. As a result of the centrifugation, erythrocytes are precipitated, and platelets are concentrated between the erythrocytes and the supernatant plasma. Subsequently, the platelets and plasma are transferred to another 10-mL centrifuge tubes, and centrifuged at 3,600 rpm for 15 minutes to precipitate the platelets. The platelets are suspended in a minimum quantity of plasma and collected, and the fraction is used as platelet-rich plasma. The platelet-rich plasma of the present invention may be a fresh one collected from a patient, or a cryopreserved one. As described below, the platelet-rich plasma may be used under any conditions as long as cell migration from the periosteum piece is promoted. For example, the platelet-rich plasma may be dropped directly on a periosteum piece, and incubated in a saturated water vapor atmosphere composed of 5% $CO_2$ and 95% air at 37° C. for 20 to 30 minutes thereby coagulating the platelet-rich plasma so as to cover the surface of the periosteum piece. Alternatively, the platelet-rich plasma may be added in the proportion of about 0.5% to a culture medium such as Medium 199 containing 10% fetal bovine serum, and used as the first culture medium. The amount and exchange frequency of the culture medium are not particularly limited as long as cell migration from the periosteum piece and cell proliferation on the substrate in the culture dish are promoted. For example, when a 100-mm diameter dish is used, 5 mL of the first culture medium is added at the beginning of culture, thereafter 10 mL of the first culture medium is added. The exchange frequency of the culture medium may be two times a week.

The first culture medium may be supplemented with a transforming growth factor beta. The transforming growth factor beta is preferably a preparation produced by recombinant DNA technologies, rather than a preparation purified from an animal, thereby avoiding the risk of infection to BSE or other diseases. Transforming growth factor beta is commercially available from various manufacturers such as PeproTech Inc. (Immuno-Biological Laboratories Co., Ltd.), Japan Becton, Dickinson and Company, and R&D Systems, Inc. (Cosmo Bio Co., Ltd.). The concentration of the transforming growth factor beta in the first culture medium is not particularly limited as long as cell migration from the periosteum piece to the substrate in the culture dish is promoted. For example, the concentration of the transforming growth factor beta may be 1 ng/mL. The transforming growth factor beta is a gene family member such as TGF $\beta1$, TGF $\beta2$ and TGF $\beta3$. In the present invention, the transforming growth factor beta may be any of the gene family members, but is preferably TGF $\beta1$.

The second culture medium is supplemented with a basic fibroblast growth factor (b-FGF). The basic fibroblast growth factor is preferably a preparation produced by recombinant DNA technologies, rather than a preparation purified from an animal, thereby avoiding the risk of infection to BSE or other diseases. The basic fibroblast growth factor is commercially available from various manufacturers such as PeproTech Inc. (Immuno-Biological Laboratories Co., Ltd.), Japan Becton, Dickinson and Company, and R&D Systems, Inc. (Cosmo Bio Co., Ltd.). The concentration of the basic fibroblast growth factor in the second culture medium is not particularly limited as long as cell migration from the periosteum piece to the substrate in the culture dish is promoted. For example, the concentration of the basic fibroblast growth factor may be from 5 to 10 ng/mL. The amount and exchange frequency of the culture medium are not particularly limited as long as proliferation of cells, which have been migrated from a periosteum piece, on the substrate in the culture dish is promoted. For example, 10 mL of the second culture medium is placed in a 10-mm diameter dish, and replaced twice a week. The timing for switching the first culture medium to the second culture medium is not particularly limited, as long as the number of cells migrated from a periosteum piece to the culture dish and proliferated is sufficient for autologous transplantation for returning the cells to the patient. For example, the first culture medium may be switched to the second culture medium after the migration to the culture dish has occurred all around the periosteum piece.

The third culture medium is supplemented with an osteoblast differentiation inducing agent. Differentiation into osteoblasts is assessed on the basis of the increase in alkaline phosphatase activity. The osteoblast differentiation inducing agent is comprised of at least one compound selected from the group consisting of dexamethasone, vitamin C, and β-glucerophosphate. The osteoblast differentiation inducing agent may be used in combination of single agents purchased from Sigma-Aldrich Corporation, Calbiochem, or other manufacturers, or a combined reagent such as StemXVivo (trade name), which is an osteogenic supplement commercially available from R&D Systems, Inc. (Cosmo Bio Co., Ltd.). The concentration of the osteoblast differentiation inducing agent in the culture medium is not particularly limited as long as the differentiation into osteoblasts is achieved. For example, the concentrations of dexamethasone, vitamin C, and β-glucerophosphate are 10 nM, 25 μg/mL, and 2 mM, respectively. The amount and exchange frequency of the culture medium are not particularly limited as long as the expression of alkaline phosphatase by the cells, which have been migrated from a periosteum piece and proliferated, is promoted on the substrate in the culture dish. For example, 10 mL of the second culture medium is placed in a 10-mm diameter dish, and replaced twice a week. The timing for switching the second culture medium to the third culture medium is not particularly limited, as long as the number of periosteum-derived cells proliferated in the culture in the second culture medium is enough for autologous transplantation for returning the cells to the patient. For example, the second culture medium may be switched to the third culture medium when the periosteum-derived cells are proliferated to reach a diameter of about 60 mm. FIG. 1 shows the order of use of the first to third culture media, and the supplements added to the respective culture media.

The culture dish and other vessels are not particularly limited as long as the risk of infection to BSE or other diseases is avoided when the cells cultured by the method for culturing human periosteum of the present invention are finally returned to the body of the patient from which the cells have been collected. For example, 100-mm diameter tissue culture dishes such as TPP, FALCON (Japan Becton, Dickinson and Company), or NUNC (Nalge Nunc International K.K.) sterilized by γ-irradiation may be used.

The periosteum piece of the present invention dissected from a patient is placed on a piece of gauze moistened with a culture solution, and aseptically transferred to a culture chamber, where aseptically pretreated and cultured, and finally autotransplanted to the patient.

Before culturing the periosteum piece of the present invention, the periosteum piece may be subjected to lysis of erythrocytes and adhesion to the culture dish. The lysis of erythrocyte, which is also referred to as hemolysis, is treatment for preventing the inclusion of many erythrocytes causing the inhibition of adhesion between the periosteum piece and the culture dish. The lysis of erythrocytes may be carried out by treating the periosteum piece with a small amount of $NH_4Cl$ solution containing no fixing agent, such as VersaLyse Lysing Solution (trade name, Beckman Coulter, Inc.) or PharmLyse (trade name, Pharmingen, BD Bioscience Clontech, Japan Becton, Dickinson and Company) for a short period of time (within 3 minutes), followed by washing with PBS three times. After washing with PBS, the periosteum piece may be incubated on a dry culture dish in a saturated water vapor atmosphere containing 5% $CO_2$ and 95% air at 37° C. for 20 to 30 minutes to evaporate excessive moisture, thereby adhering the periosteum piece to the culture dish.

Immediately after the periosteum piece is placed on the culture dish, or after the periosteum piece is adhered to the culture dish by incubation, tissue culture may be initiated upon the addition of the first culture medium. Alternatively, before the addition of the first culture medium, coating with platelet-rich plasma may be carried out. The coating with platelet-rich plasma may be carried out by dropping the platelet-rich plasma on the surface of the periosteum piece adhered to the culture dish, and then coagulating the platelet-rich plasma into a gel so as to cover the periosteum piece. The coagulation may be carried out by incubating the periosteum piece, onto which the platelet-rich plasma has been poured, in a saturated water vapor atmosphere containing 5% $CO_2$ and 95% air for 20 to 30 minutes. The coating of the periosteum piece with the platelet-rich plasma induces migration of cells with plurality of layers, which allows culturing the periosteum-derived cells so that the inherent anatomical structure of the periosteum would be relatively maintained.

Differentiation of the human periosteum-derived cells of the present invention into osteoblasts is assessed on the basis of the increase in alkaline phosphatase activity. The reason for this is that the mineralization of bone tissue is dependent on alkaline phosphatase activity. Alkaline phosphatase activity can be measured by extracting alkaline phosphatase enzyme from the cells, and determining the color reaction product by colorimetry. Alternatively, the cells may be fixed, and the localization of the insoluble reaction product of alkaline phosphatase or the localization of enzyme protein derived from anti-alkaline phosphatase antibody may be detected.

The osteoblasts of the present invention refer to the cells which express alkaline phosphatase in a test tube, and mineralize the bone tissue in vivo. The substrate employed in the method for using osteoblasts of the present invention is a scaffold for the osteoblasts of the present invention to build a three-dimensional tissue, and is formed with a porous hydroxyapatite block, hydroxyapatite granules, a platelet-rich plasma, or other inorganic and/or organic substance. The substrate of the present invention is preferably biocompatible. The artificial bone of the present invention is made by embedding the osteoblasts of the present invention in a substrate with the intention of treating bone lesion caused by periodontal disease or other causes.

(Bioethics)

Before the use of human-derived periodontal membrane cells, the protocol, which had been prepared on the basis of the code of ethics used in Niigata University Medical & Dental Hospital, was approved by the Ethics Committee of Faculty of Dentistry, Niigata University (May 9, 2005, Jun. 22, 2006). Further, in order to obtain informed consent, explanations were given to patients on as-needed basis about the collection of the periodontal ligament cells from the periodontal ligament tissue and the use of the cells in experiments, and their consents were obtained.

BEST MODE FOR CARRYING OUT THE INVENTION

Figure 1:
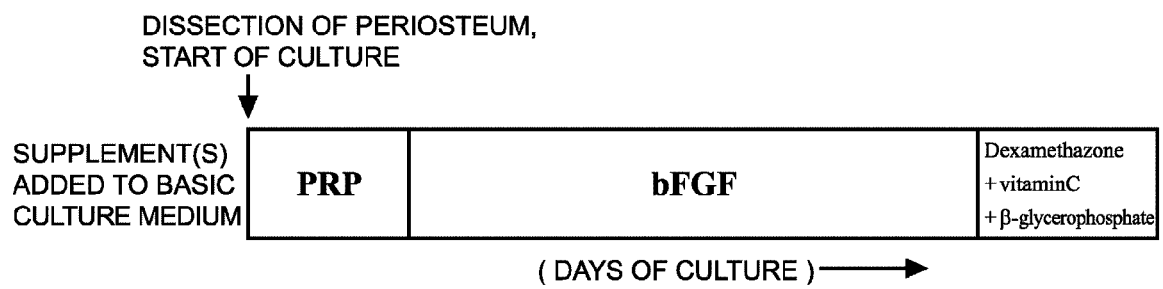
FIG. 1 is a schematic drawing showing the order of use of the first to third culture media and the supplements added to the respective culture media.

The present invention is further described below in detail with reference to examples, but the present invention will not be limited to these examples.

Example 1

1. Transfer and Pretreatment of Dissected Periosteum Tissue

The dissected periosteum tissue was, in accordance with the original method, placed on gauze moistened with a medium, aseptically transferred to an incubation room, and subjected to the following manipulation in a laminar flow cabinet. The periosteum piece was subjected to lysis of erythrocytes using VersaLyse Lysing Solution (trade name, Beckman Coulter, Inc.) for up to 3 minutes. After washing with PBS three times, the periosteum piece was placed at the center of a 100-mm diameter dish (TPP, #93100). Thereafter, the periosteum piece was incubated in a $CO_2$ incubator for about 20 to 30 minutes to remove excessive moisture, and then adhered onto the dish.

2. Adhesion of the Periosteum Piece to Culture Dish and Treatment of Platelet-Rich Plasma Platelet-rich plasma fraction was collected from the blood of a patient from whom the periosteum piece had been dissected. The fresh whole blood collected from the patient was placed in 10-mL centrifuge tubes containing an anticoagulant comprising citric acid and glucose, and centrifuged with a swing bucket rotor having a shortest axis of about 57 mm and a longest axis of about 140 mm at 2,400 rpm for 10 minutes. Upon centrifugation, erythrocytes were precipitated, and platelets were concentrated between the erythrocytes and the supernatant plasma. Subsequently, the platelets and plasma were transferred to another 10-mL centrifuge tubes, and centrifuged at 3,600 rpm for 15 minutes to precipitate the platelets. The platelets were suspended in a minimum quantity of plasma, and the collected fraction was used as platelet-rich plasma. Only 10 to 20 μL of the platelet-rich plasma was dropped on the surface of the periosteum piece, and incubated for 20 to 30 minutes. After the platelet-rich plasma was coagulated into a gel, 5 mL of the first culture medium was added, the first culture medium being Medium 199 supplemented with 0.5% platelet-rich plasma, 100 units/mL penicillin G potassium salt, 0.1 mg/mL streptomycin, 0.25 μg/mL amphotericin B (a 100-fold dilution of Antibiotic-Antilnycotic (100×) liquid (#15240-062, Invitrogen Japan K.K.), and 25 μg/mL vitamin C, and 10% Australian fetal bovine serum.

The culture conditions for promoting cell migration from the periosteum piece were studied using the following conditions (A) to (F). The condition (A) comprised the addition of the first culture medium containing no platelet-rich plasma and no growth factor (hereinafter referred to as "control"), without going through the steps of dropping of platelet-rich plasma of the patient on the surface of the periosteum piece on the culture dish and coagulating the platelet-rich plasma so as to cover the surface of the periosteum piece (hereinafter referred to as "PRP coating"). The condition (B) comprised the addition of the first culture medium supplemented with 5 ng/mL basic fibroblast growth factor (Recombinant Human FGF-basic (#100-18B), PeproTech Inc., Immuno-Biological Laboratories Co., Ltd.) (hereinafter referred to as "bFGF") without going through the step of PRP coating. The condition (C) comprised the addition of the first culture medium supplemented with 1 ng/mL transforming growth factor beta (TGF β1, R&D Systems) (hereinafter referred to as "TGF β1"), without goring through the step of PRP coating. The condition (D) comprised the PRP coating and the addition of the first culture medium containing no platelet-rich plasma and no growth factor (hereinafter referred to as "PRP"). The condition (E) comprised the PRP coating and the addition of the first culture medium supplemented with 5 ng/mL basic fibroblast growth factor (hereinafter referred to as "PRP+bFGF"). The condition (F) comprised the PRP coating and the addition of the first culture medium containing 1 ng/mL transforming growth factor beta 1 (hereinafter referred to as "PRP+TGF β1").

3. Timing for Replacement of Culture Medium

The culture medium was replaced twice a week. The volume of the culture medium in a 100-mm diameter culture dish was 5 mL at the beginning of culture, and was increased to 10 mL after the first replacement of the culture medium. On day 7 of culture, the first culture medium was switched to the second culture medium which was Medium 199 culture medium containing 5 to 10 mg/mL basic fibroblast growth factor (Recombinant Human FGF-basic (#100-18B), PeproTech Inc., Immuno-Biological Laboratories Co., Ltd.), 100 unit/mL penicillin G potassium salt, 0.1 mg/mL streptomycin, 0.25 μg/mL amphotericin B (a 100-fold dilution of Antibiotic-Antimycotic (100×) liquid (#15240-062, Invitrogen Japan K.K.)), 25 μg/mL vitamin C, and 10% Australian fetal bovine serum. Thereafter, on day 21 of culture, the second culture medium was switched to the third culture medium which was Medium 199 culture medium supplemented with 10 nM dexamethasone, 25 μg/mL vitamin C, 2 mM β-glucerophosphate, 100 units/mL penicillin G potassium salt, 0.1 mg/mL streptomycin, 0.25 μg/mL amphotericin B (a 100-fold dilution of Antibiotic-Antimycotic (100×) liquid (#15240-062, Invitrogen Japan K.K.), and 10% Australian fetal bovine serum.

4. Histochemical Detection of ALP Activity and Mineralized Product

In order to detect ALP activity, the cells were fixed with 10% neutral formalin, and treated with a commercially available kit (Alkaline Phosphatase Staining Kit, Muto Pure Chemicals Co., Ltd.). In brief, after rinsing the culture dish with PBS, the cells were fixed with formalin, and subjected to enzyme reaction using naphthol AS-MX phosphate as a substrate and a fast blue RR salt as a diazonium salt, thereby detecting the localization of the enzyme by the insoluble blue reaction product. The cells were counter-stained with 1% safranine O to reddish purple.

5. Results (1) Cell Migration from Periosteum Piece

Figure 2:
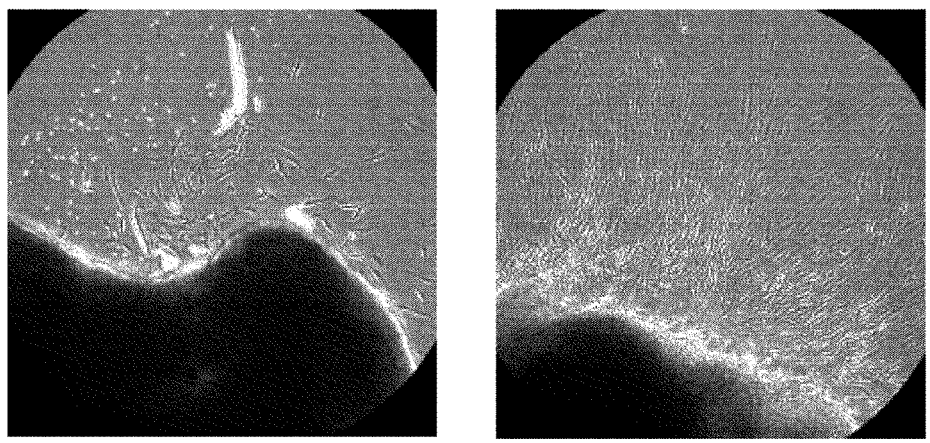
FIG. 2 lists optical micrographs showing cell migration from a periosteum piece on day 5 of culture.

FIG. 2 lists phase contrast micrographs showing cell migration from a periosteum piece on day 5 of culture. The right is a phase contrast micrograph showing the result of culturing the periosteum piece, which had been subjected to lysis of erythrocytes and coating with platelet-rich plasma, in the first culture medium supplemented with 0.5% platelet-rich plasma according to the method for culturing human periosteum of the present invention. In the micrograph, cell migration is observed in all around the periosteum piece, the migration distance being 1 mm or more from the periosteum piece. The left is a phase contrast micrograph showing the result of culturing the control periosteum piece, which had not been subjected to lysis of erythrocytes or coating with platelet-rich plasma, in a culture medium containing no platelet plasma. In the micrograph, cell migration is found only from a portion of the perimeter of the periosteum piece, the migration distance being 0.1 to 0.2 mm.

Figure 3:
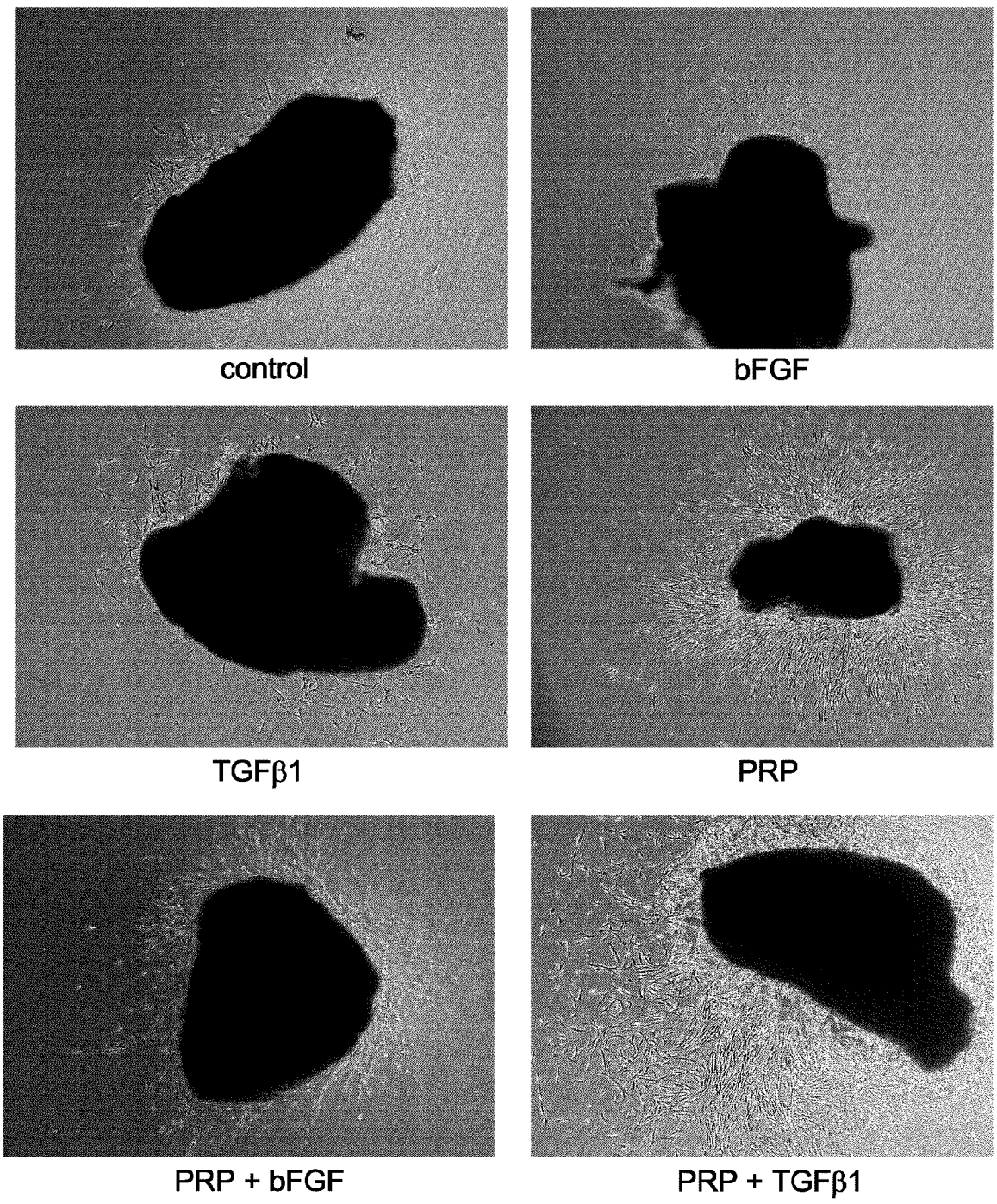
FIG. 3 lists optical micrographs showing the proliferation of cells migrated from a periosteum piece on day 5 of culture under various conditions.

(2) Study of Culture Conditions for Promoting Cell Migration from Periosteum Piece FIG. 3 lists phase contrast micrographs showing cell migration from the periosteum pieces on day 5 of culture under various culture conditions. The periosteum piece shown at top left was cultured for 5 days under the condition (A), top right was cultured under the condition (B), middle left was cultured under the condition (C), middle right was cultured under the condition (D), bottom left was cultured under the condition (E), and bottom right was cultured under the condition (F). When the periosteum piece, which had been subjected to PRP coating, was cultured in the first culture medium containing no growth factor (condition (D), middle right in FIG. 3) showed active cell migration in the same manner as in FIG. 2. On the other hand, when no PRP coating was carried out, cell migration barely occurred in the culture in the first culture medium supplemented with the basic fibroblast growth factor (condition (B), top right in FIG. 3) or the culture in the first culture medium containing the transforming growth factor beta 1 (condition (C), middle left in FIG. 3), just as with the control culture in the first culture medium containing no growth factor (condition (A), top left in FIG. 3). When the PRP coating was carried out, the degree of cell migration was almost the same between the culture in the first culture medium supplemented with the basic fibroblast growth factor (condition (E), bottom left in FIG. 3) and the culture in the first culture medium containing no growth factor (condition (D), middle right in FIG. 3). On the other hand, cell migration was promoted in the culture in the first culture medium supplemented with the transforming growth factor beta 1 (condition (F), bottom left in FIG. 3), in comparison with the culture in the first culture medium containing no growth factor (condition (D), middle right in FIG. 3). These test results have shown that the step of dropping the platelet-rich plasma of the patient on the surface of the periosteum piece on the culture dish and coagulating the platelet-rich plasma so as to cover the surface of the periosteum piece (PRP coating) according to the method for culturing the piece of human periosteum tusse of the present invention cannot be replaced with a culture medium supplemented with a basic fibroblast growth factor or a transforming growth factor beta. Also found is that, when PRP coating is carried out, the addition of a basic fibroblast growth factor does not promote cell migration, but the addition of a transforming growth factor beta 1 promotes cell migration in comparison with the culture in a culture medium containing no growth factor.

(3) Cell Proliferation on Culture Dish

Figure 4:
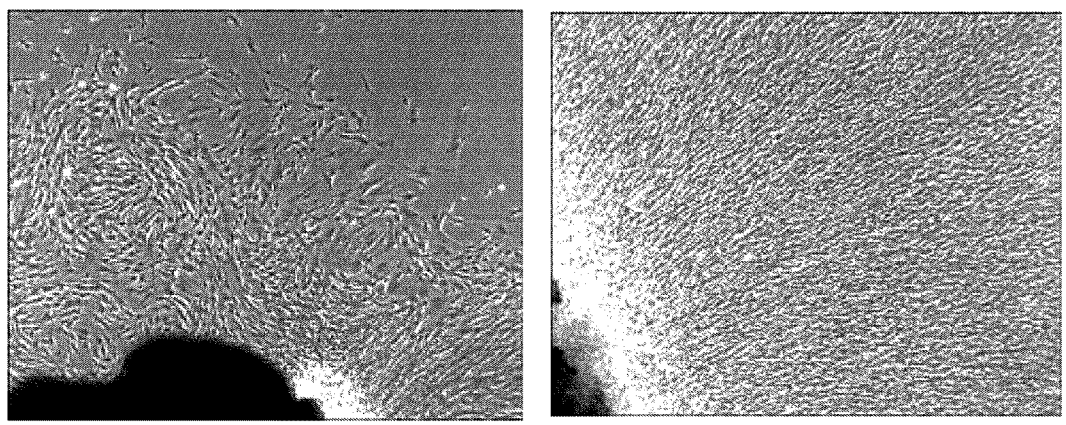
FIG. 4 lists optical micrographs showing the proliferation of cells migrated from a periosteum piece on day 15 of culture.

FIG. 4 lists phase contrast micrographs showing the proliferation of periosteum piece cells on day 15 of culture. The right is a phase contrast micrograph showing the result achieved by the periosteum culture method of the present invention, wherein the periosteum piece, which had been subjected to lysis of erythrocytes and coating with platelet-rich plasma, was cultured for 1 week in the first culture medium supplemented with 0.5% platelet-rich plasma, and then cultured for another 8 days in the second culture medium containing 10 ng/mL basic fibroblast growth factor. Marked cell proliferation is observed in the micrograph. The left is a phase contrast micrograph showing the result of culturing the control periosteum piece, which had not been subjected to lysis of erythrocytes or coating with platelet-rich plasma, for 15 days in the culture medium containing no supplement. Poor migration and proliferation of the cells are observed in the micrograph.

(4) Expression of Alkaline Phosphatase

Figure 5:
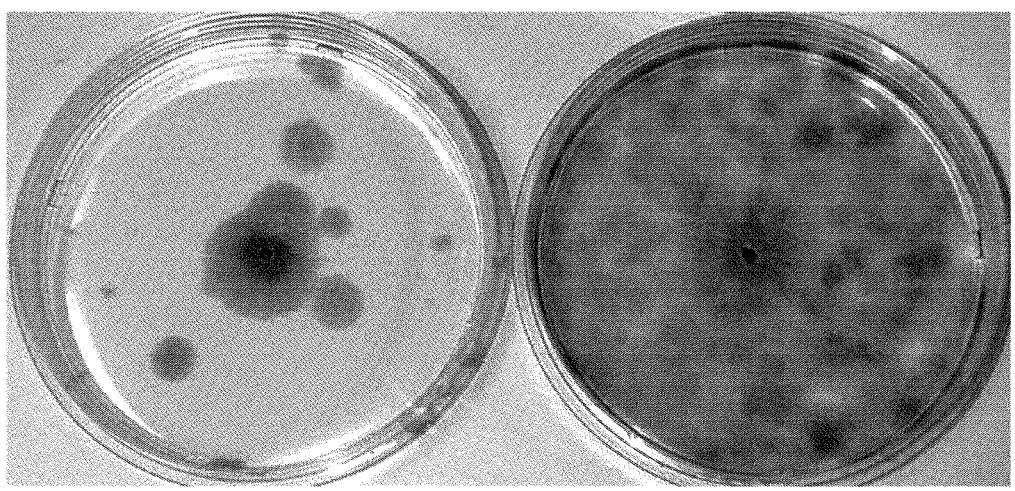
FIG. 5 is a photograph showing the expression of alkaline phosphatase on a cultured periosteum sheet fixed and stained on day 27 of culture.

FIG. 5 is a photograph showing the expression of alkaline phosphatase on the cultured periosteum sheet which had been fixed and stained on day 27 of culture. Pale gray areas indicate cells, and dark gray areas indicate the regions where alkaline phosphatase activity was detected. The right shows the result of staining of the culture dish wherein the periosteum piece, which had been subjected to lysis of erythrocytes and coating with platelet-rich plasma, was cultured for 1 week in the first culture medium containing 0.5% platelet-rich plasma, thereafter cultured for 2 weeks in the second culture medium supplemented with 10 ng/mL basic fibroblast growth factor, and then further cultured for 5 days in the third culture medium supplemented with 10 nM dexamethasone, 25 µg/mL vitamin C, and 2 mM β-glucerophosphate in accordance with the periosteum culture method of the present invention. The result shows marked cell proliferation and strong alkaline phosphatase activity. The left is the result of staining of the culture dish wherein the control periosteum piece, which had not been subjected to lysis of erythrocytes or coating with platelet-rich plasma, was cultured for 27 days in a culture medium containing no supplement; alkaline phosphatase activity was slightly observed.

The average diameter of the periosteum sheets grown by the periosteum culture method of the present invention was about 60 mm on day 20 of culture, and 90 to 100 mm on day 27 of culture. On the other hand, the average diameter of the periosteum sheets grown by prior art culture method was only about 60 mm on day 45 of culture. These results demonstrate that the culture method of the present invention achieves a 50% or more reduction on the period of culture time in comparison with prior art culture method.

The invention claimed is:

1. A method for culturing a piece of human periosteum tissue to grow a periosteum sheet, comprising the steps of:
   (1) subjecting a periosteum piece dissected from a patient to lysis of erythrocytes, washing with saline, and placing on a dry culture dish containing no culture solution;
   (2) dropping platelet-rich plasma collected from the patient onto the surface of the periosteum piece on the culture dish and coagulating the platelet-rich plasma so as to cover the surface of the periosteum piece, wherein the platelet-rich plasma induces migration of periosteum-derived cells outwardly from the periosteum piece in the culture dish;
   (3) growing the cells by adding a first culture medium to the culture dish after the step (2), wherein the first culture medium is supplemented with at least one transforming growth factor beta selected from the group consisting of transforming growth factor beta 1, transforming growth factor beta 2, and transforming growth factor beta 3; and
   (4) growing the cultured cells in a second culture medium containing basic fibroblast growth factor and no platelet-rich plasma, after the step (3); and obtaining the periosteum sheet of an average diameter of about 90 to 100 mm grown around the periosteum piece in 27 days.

2. The method for culturing the piece of human periosteum tissue according to claim 1, wherein the transforming growth factor beta is transforming growth factor beta 1.

3. The method for culturing the piece of human periosteum tissue according to claim 1, wherein the step (4) is followed by a step (5) of growing the periosteum sheet in a third culture medium supplemented with an osteoblast differentiation inducing agent, wherein the osteoblast differentiation inducing agent comprises dexamethasone, vitamin C, and beta-glycerophosphate.

* * * * *